(12) United States Patent
Jackson

(10) Patent No.: US 11,000,314 B2
(45) Date of Patent: *May 11, 2021

(54) CANNULATED POLYAXIAL SCREW

(71) Applicant: Roger P. Jackson, Prairie Village, KS (US)

(72) Inventor: Roger P. Jackson, Prairie Village, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 15/723,972

(22) Filed: Oct. 3, 2017

(65) Prior Publication Data
US 2018/0021067 A1    Jan. 25, 2018

Related U.S. Application Data

(63) Continuation of application No. 14/868,213, filed on Sep. 28, 2015, now Pat. No. 9,808,292, which is a
(Continued)

(51) Int. Cl.
*A61B 17/70* (2006.01)

(52) U.S. Cl.
CPC ...... *A61B 17/7037* (2013.01); *A61B 17/7032* (2013.01)

(58) Field of Classification Search
CPC ............ A61B 17/7032; A61B 17/7037; A61B 7/1604; A61B 7/1703; A61B 7/1671;
(Continued)

(56) References Cited

U.S. PATENT DOCUMENTS 1,646,143 A   10/1927 Forster
5,312,404 A   5/1994 Asher et al.
(Continued)

FOREIGN PATENT DOCUMENTS

DE   19507141      9/1996
DE   20207850 U1  10/2002
(Continued)

OTHER PUBLICATIONS

European Search Report, EP14189707.4, dated Feb. 25, 2015.
(Continued)

*Primary Examiner* — Pedro Philogene
(74) *Attorney, Agent, or Firm* — Polsinelli PC

(57) ABSTRACT

A polyaxial bone screw having a bone implantable shank, a head and a retaining ring. The retaining ring includes an outer partial hemispherical surface and an inner bore with radially extending channels and partial capture recesses. The shank includes a bone implantable body with an external helical wound thread and an upwardly extending capture structure. The capture structure includes at least one spline which extends radially outward and has a wedged surface that faces radially outward therefrom. The capture structure operably passes through a central bore of the retaining ring while the spline passes through a suitably shaped channel so that the spline becomes positioned above the head at which time the shank is rotated appropriately and the shank is drawn back downwardly so that the spline engages and seats in the capture recess. The head includes an internal cavity having a spherical shaped surface that mates with the ring surface and has a lower restrictive neck that prevents passage of the ring once the ring is seated in the cavity.

37 Claims, 7 Drawing Sheets

Related U.S. Application Data continuation-in-part of application No. 13/068,505, filed on May 12, 2011, now Pat. No. 9,144,444, which is a continuation of application No. 12/290,244, filed on Oct. 29, 2008, now Pat. No. 7,967,850, and a continuation-in-part of application No. 10/818,555, filed on Apr. 5, 2004, now Pat. No. 8,052,724, which is a continuation of application No. 10/464,633, filed on Jun. 18, 2003, now Pat. No. 6,716,214.

(60) Provisional application No. 61/000,964, filed on Oct. 30, 2007.

(58) Field of Classification Search
CPC ..... A61B 7/1757; A61B 7/701; A61B 7/7011; A61B 7/7035; A61B 7/708; A61B 7/7082; A61B 7/7083; A61B 7/7085; A61B 7/7091; A61B 7/8605; A61B 7/861; A61B 7/8863; A61B 7/8897; A61B 7/00234; A61B 7/8866; A61B 7/8875; A61B 7/1655; A61B 2090/037; A61B 2090/061; A61B 2090/062; A61B 2090/031; Y10S 606/914
USPC .............. 606/246–279, 300–328, 96 A, 914
See application file for complete search history.

(56) References Cited

U.S. PATENT DOCUMENTS

| | | | |
|---|---|---|---|
| 5,360,431 | A | 11/1994 | Puno et al. |
| 5,429,639 | A | 7/1995 | Judet |
| 5,443,467 | A | 8/1995 | Biedermann et al. |
| 5,466,237 | A * | 11/1995 | Byrd, III ............ A61B 17/7037 606/272 |
| 5,476,464 | A | 12/1995 | Metz-Stavenhagen et al. |
| 5,545,163 | A * | 8/1996 | Miller ................ A61B 17/7007 606/287 |
| 5,562,661 | A | 10/1996 | Yoshimi et al. |
| 5,591,166 | A | 1/1997 | Bernhardt et al. |
| 5,601,553 | A | 2/1997 | Trebing et al. |
| 5,667,508 | A | 9/1997 | Errico et al. |
| 5,669,911 | A * | 9/1997 | Errico ................ A61B 17/7034 606/264 |
| 5,672,176 | A | 9/1997 | Biedermann et al. |
| 5,690,630 | A | 11/1997 | Errico et al. |
| 5,716,356 | A | 2/1998 | Biedermann et al. |
| 5,725,528 | A | 3/1998 | Errico et al. |
| 5,733,286 | A | 3/1998 | Errico et al. |
| 5,782,833 | A | 7/1998 | Haider |
| 5,800,435 | A | 9/1998 | Errico et al. |
| 5,817,094 | A | 10/1998 | Errico et al. |
| 5,879,350 | A | 3/1999 | Sherman et al. |
| 5,891,145 | A | 4/1999 | Morrison et al. |
| 5,899,906 | A | 5/1999 | Schenk |
| 5,954,725 | A | 9/1999 | Sherman et al. |
| 6,019,759 | A | 2/2000 | Rogozinski |
| 6,050,997 | A | 4/2000 | Mullane |
| 6,063,090 | A * | 5/2000 | Schlapfer ........... A61B 17/7037 606/270 |
| 6,074,391 | A | 6/2000 | Metz-Stevanhagen et al. |
| 6,077,262 | A | 6/2000 | Schlapfer et al. |
| 6,090,110 | A | 7/2000 | Metz-Stavenhagen |
| 6,090,111 | A | 7/2000 | Nichols |
| 6,132,432 | A | 10/2000 | Richelsoph |
| 6,146,383 | A | 11/2000 | Studer et al. |
| 6,187,005 | B1 | 2/2001 | Brace et al. |
| RE37,161 | E | 5/2001 | Michelson et al. |
| 6,224,596 | B1 | 5/2001 | Jackson |
| 6,254,602 | B1 | 7/2001 | Justis |
| 6,273,888 | B1 | 8/2001 | Justis |
| 6,280,442 | B1 | 8/2001 | Barker et al. |
| 6,287,308 | B1 | 9/2001 | Betz et al. |
| 6,287,311 | B1 | 9/2001 | Sherman et al. |
| 6,302,888 | B1 | 10/2001 | Mellinger et al. |
| 6,328,739 | B1 | 12/2001 | Liu et al. |
| 6,368,321 | B1 | 4/2002 | Jackson |
| 6,488,681 | B2 * | 12/2002 | Martin ............... A61B 17/7037 606/278 |
| 6,565,565 | B1 | 5/2003 | Yuan et al. |
| 6,716,214 | B1 * | 4/2004 | Jackson ............ A61B 17/7037 606/266 |
| 6,835,196 | B2 | 12/2004 | Biedermann et al. |
| 7,250,052 | B2 * | 7/2007 | Landry ............. A61B 17/1604 606/86 A |
| 7,572,279 | B2 * | 8/2009 | Jackson ............ A61B 17/7032 606/266 |
| 7,662,175 | B2 * | 2/2010 | Jackson ............ A61B 17/7037 606/300 |
| 7,833,250 | B2 * | 11/2010 | Jackson ............ A61B 17/7037 606/270 |
| 7,967,850 | B2 | 6/2011 | Jackson |
| 8,603,145 | B2 * | 12/2013 | Forton ............... A61B 17/8605 606/251 |
| 9,144,444 | B2 | 9/2015 | Jackson |
| 10,278,740 | B2 | 5/2019 | Jackson |
| 2001/0001119 | A1 | 5/2001 | Lombardo |
| 2002/0026193 | A1 | 2/2002 | Barker et al. |
| 2003/0023240 | A1 | 1/2003 | Amrein et al. |
| 2003/0100904 | A1 | 5/2003 | Biedermann |
| 2003/0187434 | A1 | 10/2003 | Lin |
| 2003/0187439 | A1 | 10/2003 | Biedermann et al. |
| 2004/0153068 | A1 | 8/2004 | Janowski et al. |
| 2005/0216003 | A1 | 9/2005 | Biedermann et al. |
| 2005/0267472 | A1 | 12/2005 | Biedermann et al. |
| 2006/0173456 | A1 | 8/2006 | Hawkes |
| 2010/0030280 | A1 | 2/2010 | Jackson |
| 2010/0036433 | A1 | 2/2010 | Jackson |
| 2016/0183984 | A1 | 6/2016 | Jackson |
| 2017/0196610 | A1 | 7/2017 | Jackson |
| 2020/0022738 | A1 | 1/2020 | Jackson |
| 2020/0146726 | A1 | 5/2020 | Jackson |

FOREIGN PATENT DOCUMENTS

| | | |
|---|---|---|
| EP | 1121902 | 1/2001 |
| WO | WO 95/13755 | 5/1995 |

OTHER PUBLICATIONS

*EBI Omega 21 Brochure*, EBI Spine Systems, pub. 1999.
*Claris Instrumentation Brochure*, G Med, pub. 1997.
*VLS System Variable Locking Screw Brochure*, Interpore Cross International, 1999.
*The Rod Plate System Brochure*, Stryker Howmedica Osteonics, pub. Oct. 1999.
*SDRS Surgical Dynamics Rod System Brochure*, Surgical Dynamics, pub. 1998-99.
*Versalok Low Back Fixation System Brochure*, Wright Medical Technology, Inc., pub. 1997.
U.S. Appl. No. 10/561,445, dated Feb. 18, 2020, Jackson.

* cited by examiner

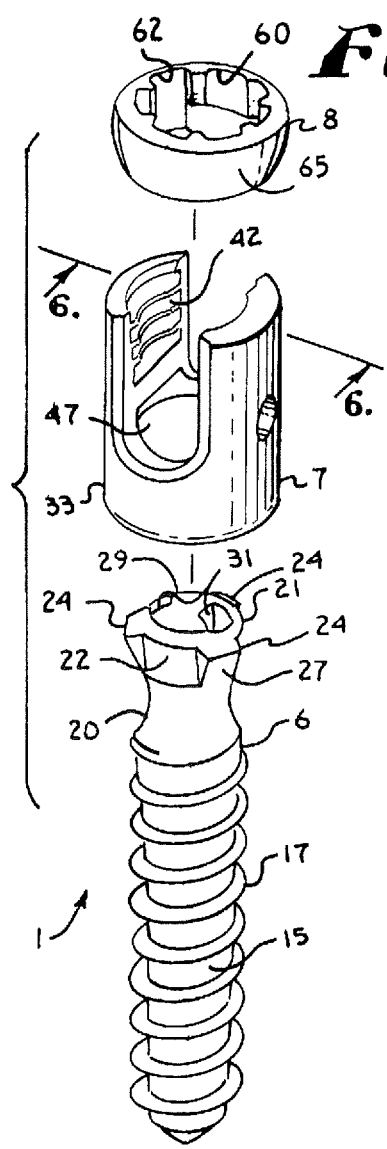
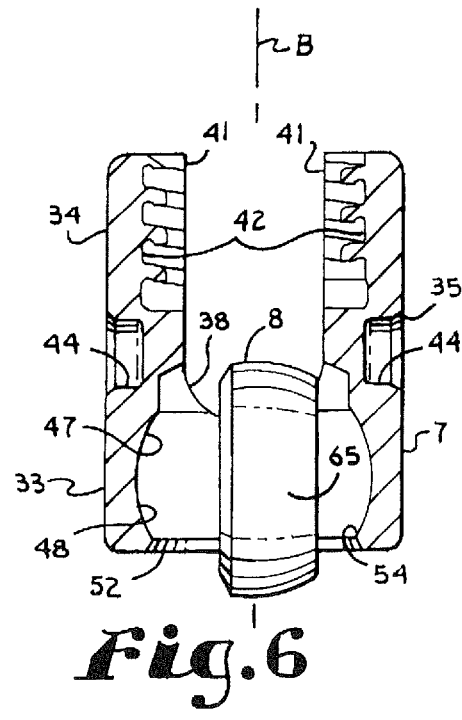
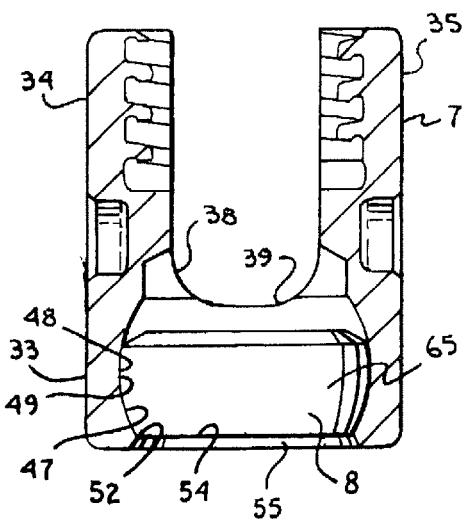

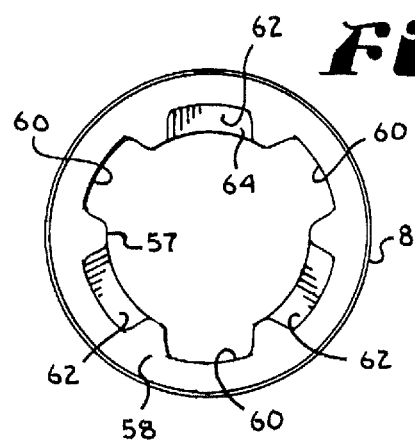
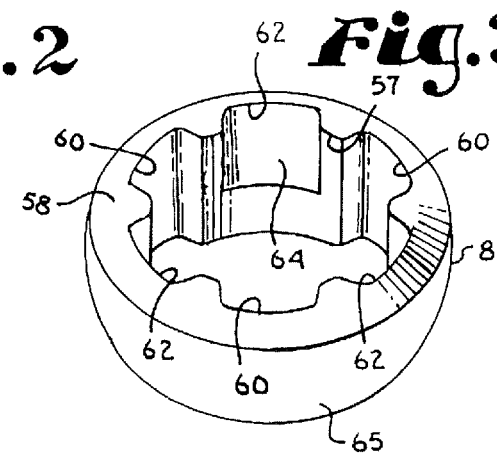
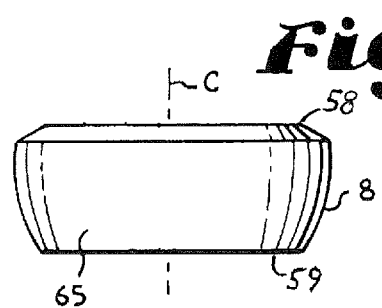
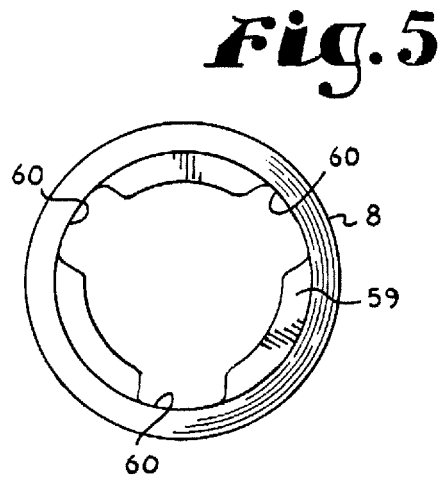

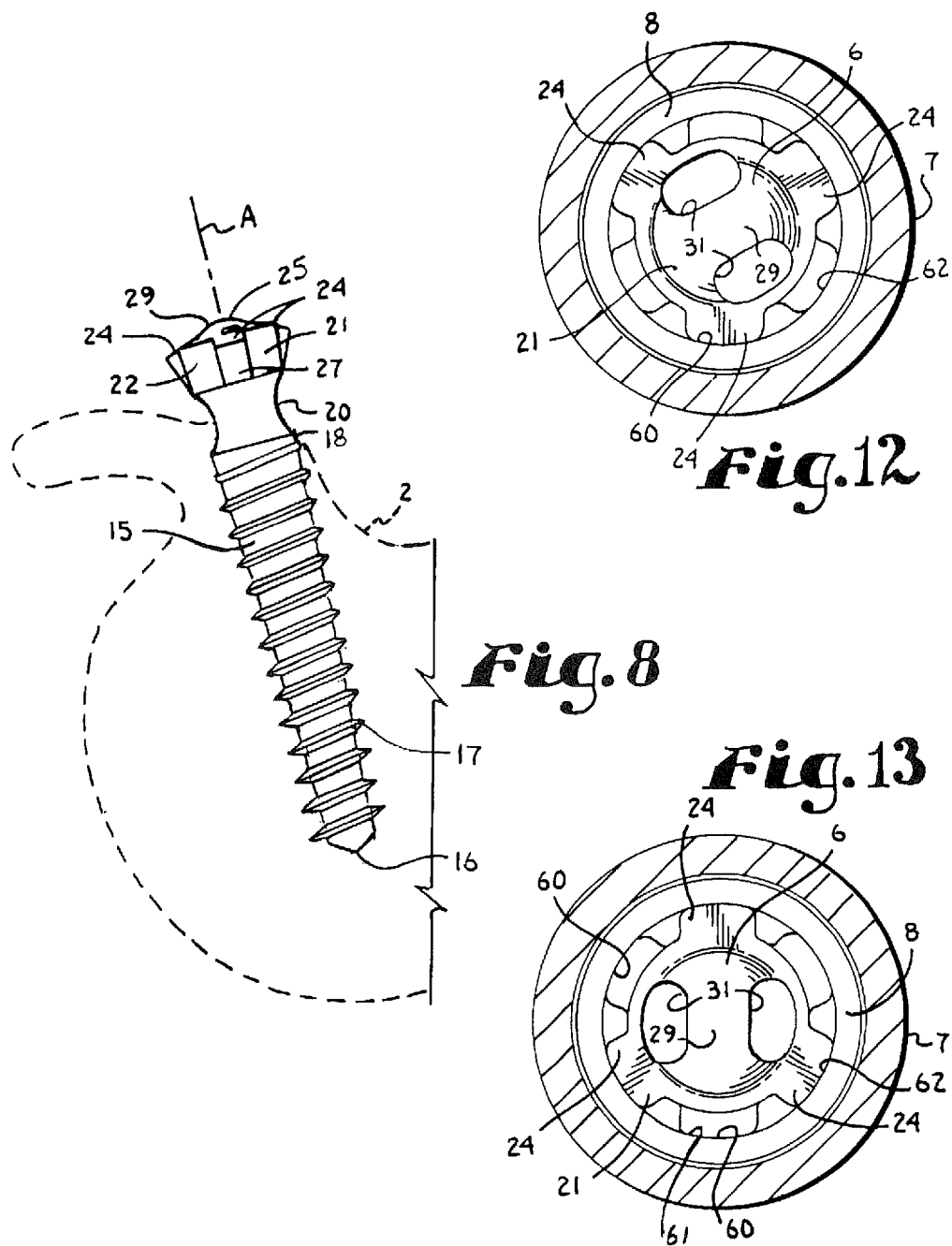

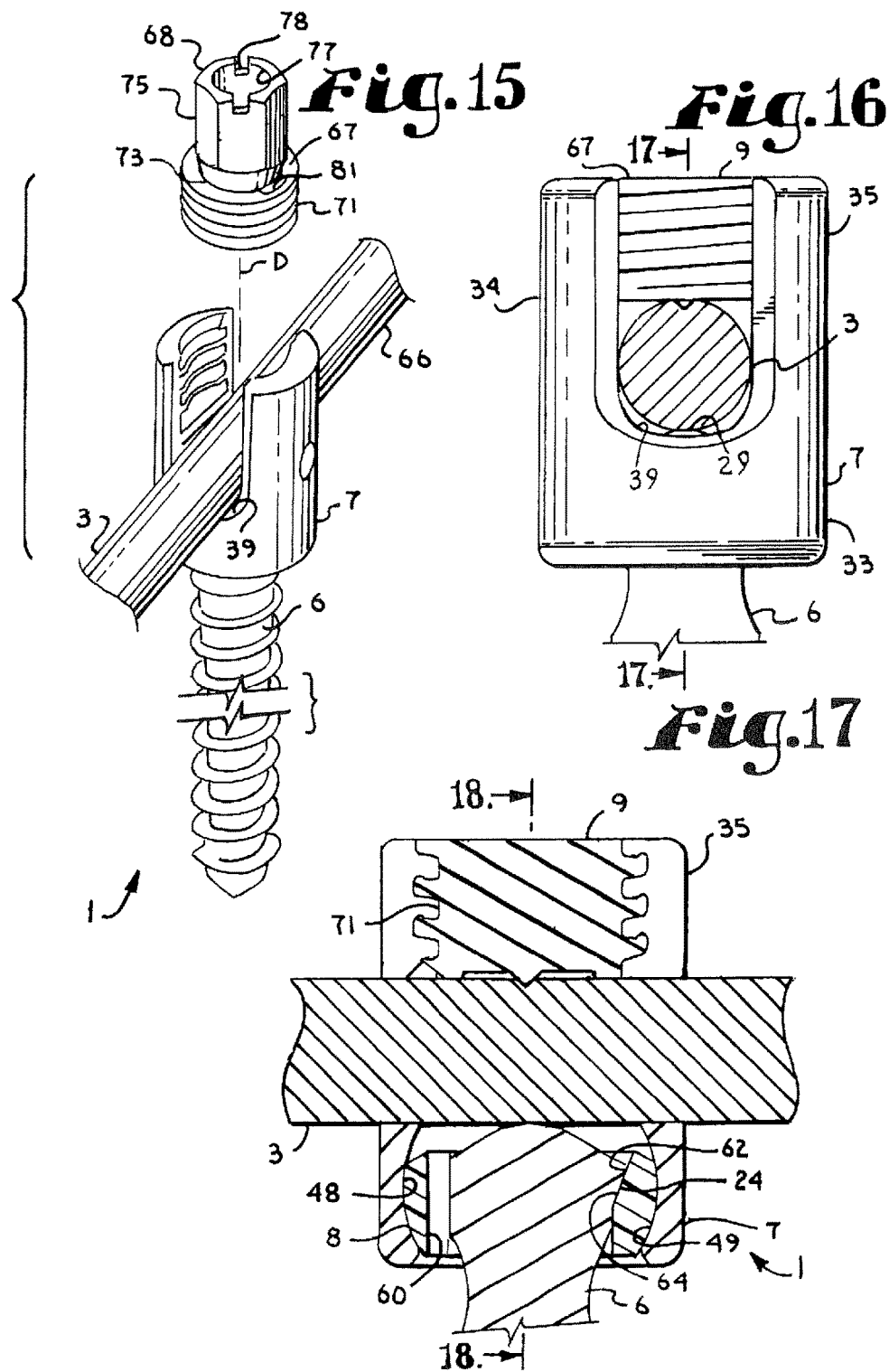

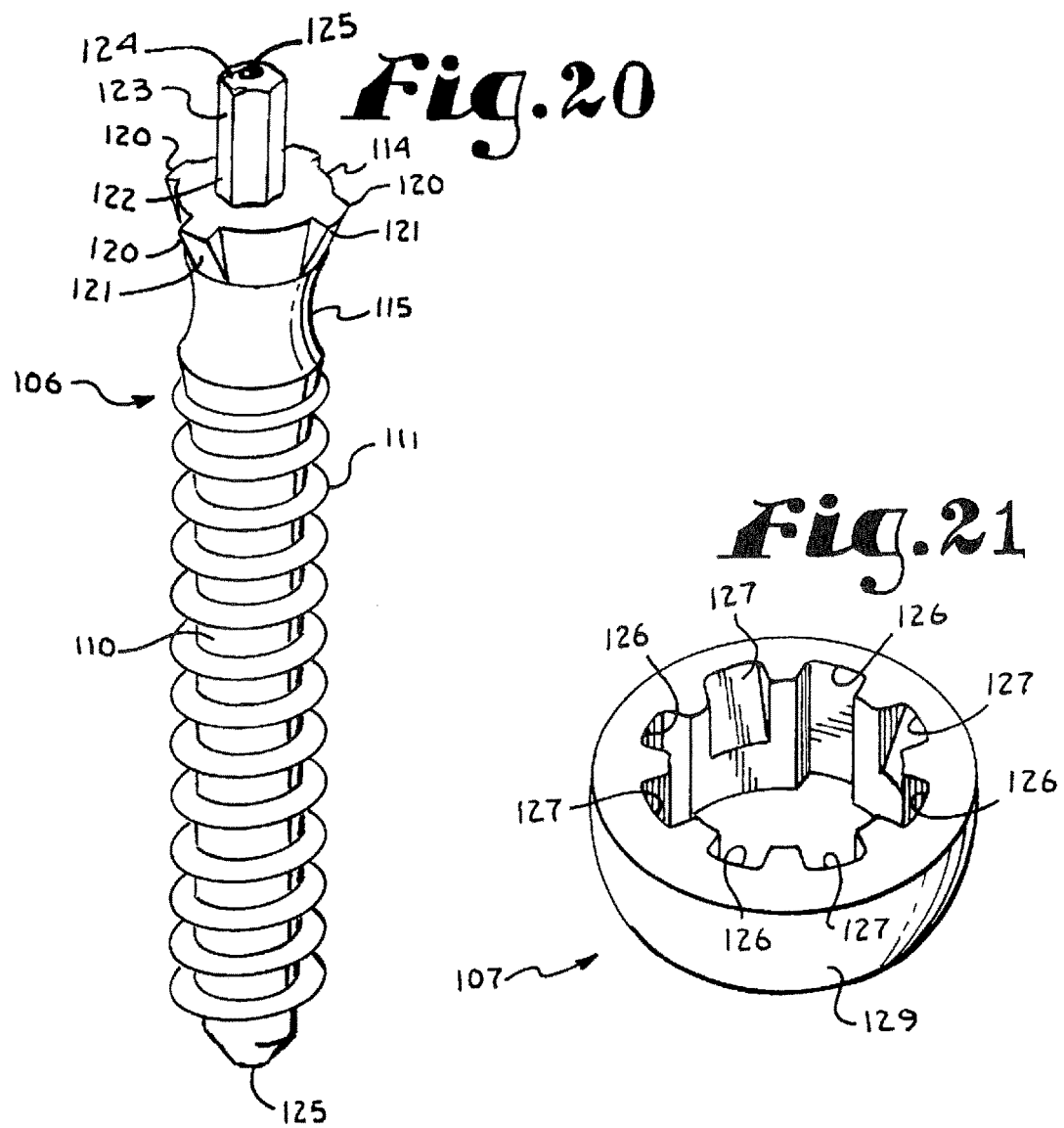

CANNULATED POLYAXIAL SCREW

CROSS-REFERENCE TO RELATED APPLICATIONS

This application is a continuation of U.S. patent application Ser. No. 14/868,213, filed Sep. 28, 2015, which is a continuation-in-part of U.S. patent application Ser. No. 13/068,505, filed May 12, 2011, now U.S. Pat. No. 9,144,444, which is a continuation of U.S. patent application Ser. No. 12/290,244, filed Oct. 29, 2008, previously U.S. Pat. No. 7,967,850, now U.S. Pat. No. RE46,431, which claims the benefit of U.S. Provisional Application No. 61/000,964, filed Oct. 30, 2007. U.S. patent application Ser. No. 12/290,244 is also a continuation-in-part of U.S. patent application Ser. No. 11/522,503, filed Sep. 14, 2006, now U.S. Pat. No. 7,766,915. U.S. patent application Ser. No. 12/290,244 is also a continuation-in-part of U.S. patent application Ser. No. 11/024,543, filed Dec. 20, 2004, now U.S. Pat. No. 7,204,838. U.S. patent application Ser. No. 12/290,244 is also a continuation-in-part of U.S. patent application Ser. No. 11/140,343, filed May 27, 2005, now U.S. Pat. No. 7,776,067. U.S. patent application Ser. No. 12/290,244 is also a continuation-in-part of application Ser. No. 10/986,377, filed Nov. 10, 2004, now U.S. Pat. No. 7,833,250. U.S. patent application Ser. No. 12/290,244 is a continuation-in-part of U.S. patent application Ser. No. 10/818,555, filed Apr. 5, 2004, now U.S. Pat. No. 8,052,724, which is a continuation of U.S. patent application Ser. No. 10/464,633, filed Jun. 18, 2003, now U.S. Pat. No. 6,716,214. Each of the foregoing applications is incorporated by reference in its entirely herein and for all purposes.

BACKGROUND OF THE INVENTION

The present invention is directed to a polyaxial bone screw for use in spinal surgery and the like and especially to such a screw adapted to receive a rod member and secure the rod member to a vertebra or the like.

Many spinal surgery procedures require securing various implants to bone and especially to vertebrae along the spine. For example, elongate rods are often required that extend along the spine to provide support to vertebrae that have been damaged or weakened due to injury, disease or the like. Such rods must be supported by certain vertebra and support other vertebra. The most common mechanism for providing such structure is to implant bone screws into certain bones which then in turn support the rod or are supported by the rod. Bone screws of this type may have a fixed head relative to a shank thereof. In the fixed bone screws, the head cannot be moved relative to the shank and the rod must be favorably positioned in order for it to be placed within the head. This is sometimes very difficult or impossible to do so polyaxial bone screws are commonly used. The polyaxial bone screws allow rotation of the head about the shank until a desired rotational position is achieved for the head relative to the shank after which the rod can be inserted and the position of the head eventually locked with respect to movement relative to the shank.

The present invention is directed to such swivel head type bone screws and, in particular, to swivel head bone screws having an open head that allows placement of the rod member within the head and then subsequent closure by use of a closure top, plug or the like to capture the rod in the head of the screw.

Because such implants are for placement within the human body, it is always desirable for the implant to have as little effect on the body as possible. Consequently, it is quite desirable for the implants to have a relatively small profile both in height and width. It is also desirable that the implants be lightweight.

Furthermore, it is desirable that the swivel head implants be unlikely to unintentionally disassemble within the body. It is very undesirable for pieces of the implant to be free to move around within the body after surgery is completed and it also assures that the implant retains an ability to correct the structural problem for which it was implanted. Furthermore, if the implant should slip or become loose for some reason, it is still desirable for all of the parts to remain together and not separate.

Consequently, it is desirable for there to be a lightweight, low profile polyaxial bone screw which assembles in such a manner that each subsequent piece locks proceeding pieces within the overall structure, so that there is less likelihood that the various pieces of the structure will undesirably disassemble.

SUMMARY OF THE INVENTION

The present invention is directed to a polyaxial bone screw that comprises a shank, a head and a retainer ring that operably cooperate with each other. The bone screw is designed to allow the shank to be locked or secured in a selected angular configuration with respect to the head, while the head receives a rod member and while the shank is implanted in a bone, such as a vertebra or vertebral body.

The shank has an implant body which includes an external helically wound thread that is in turn attached by a neck to a capture end with a capture or connector type structure. The capture structure is positioned outside the bone in use and has a radiused and cylindrically shaped radially outer surface that has at least one radially outwardly extending non helically wound projection or spline thereon. The capture structure also has an upper axially aligned and radiused dome that protrudes above the remainder of the shank and above the ring during use to manipulate the shank and to contact the rod. Further, in some embodiments the shank includes off axis apertures, grooves, side slots or the like for use by an installation tool with a mating configured head for driving and rotating the shank into the bone.

The head has a generally cylindrical shaped profile with an upwardly open U-shaped channel formed therein so as to effectively produce a lower base with two upstanding and spaced arms. The inner surfaces of the arms have a threadform thereon or another suitable guide and advancement structure such as a helically wound flangeform for use in closing the upper part of the channel. Located in the interior of the base and coaxially aligned with the head is a chamber having an interiorly facing partial spherical shaped surface. The chamber further opens onto a bottom surface of the head through a head lower wall bore forming a constricted or restrictive neck sized and shaped to allow passage of the capture structure therethrough.

The retainer ring includes an external partial spherical or hemispherical surface that is sized and shaped to be seated in and slidably engage the partial spherical surface within the head, both having approximately the same radius of generation. The ring also has an internal, centrally located and axially extending ring bore sized and shaped to receive the capture structure of the shank therethrough. Further, the ring has a series of axially extending channels positioned about and opening into the central bore that are sized and shaped to allow sliding passage of the shank splines entirely through the ring so that the shank can be inserted through the ring while the ring is positioned within the chamber in the head. The channels are not helically wound about the bore and preferably extend vertically or parallel to the axis of the ring. The ring further includes a set of recesses that are circumferentially spaced from the channels and that open onto the upper part of the ring and into the bore, but do not pass entirely through the ring and that can be entered by the splines by drawing the shank with the splines thereon axially downwardly with respect to the ring. In this manner, the splines can be passed upwardly or uploaded through the ring by sliding through the channels in conjunction with the remainder of the shank capture and after sliding completely through the bore, the shank is then rotated a certain number of degrees relative to the head, and then drawn back downwardly or downloaded so that the splines encounter and engage the recesses wherein the splines are captured by the ring. The splines preferably have a wedge-shaped surface thereon which pushes not only downwardly, but radially outward against the retainer or capture ring when force is applied to the top of the shank.

During assembly, the ring is placed through the U-shaped channel into the chamber having the partial spherical surface and then rotated so that the ring hemispherical surface mates with and slidably engages the head partial spherical surface. Subsequently, the shank capture structure is uploaded into and extended through the ring central bore, while the splines pass through the channels. The shank is then rotated relative to the ring and then the shank is moved in an axially reverse direction opposed to uploading while the splines are positioned over the recesses so as to be aligned with the recesses and not aligned with the channels and so that the splines then enter the recesses. The ring with connected shank effectively thereafter form a ball and socket joint with the head and allow free rotation to a selected angular configuration until later locked in the selected configuration. The shank, head and ring are then placed in a bone by screwing the shank body into the bone using the apertures on the top of the shank or alternative structure such as grooves or faceted surfaces on the outside of the portion of the shank extending above the ring.

Thereafter, a rod is placed in the U-shaped channel and captured therein by closing the channel by use of a closure top or plug having a threadform or other external guide and advancement structure that mates with and advances along mating guide and advancement structure of the arms of the head, when the closure top is rotated. Preferably, the closure top also includes a break-off head that provides purchase for a tool for rotation and torqueing of the closure top to a preselected torque and that such torque is transferred and applied as pressure against the rod received in the head. Once the preselected torque is achieved, the break-off head breaks away from the closure top. Under pressure from the closure top, the rod pushes against the dome of the shank that extends above the ring and thereby urges the splines downwardly. Because of the wedge shaped structure of the splines, the splines push both downwardly and outwardly upon the retainer or capture ring, when force is applied to the dome, so as to frictionally engage and positively seat the retaining ring in the cavity and prevent further rotation in conjunction with the shank dome frictionally engaging the rod under pressure. In particular, the hemispherical surface of the ring abuttingly and frictionally mates with the integral hemispherical interior facing surface of the head, while the dome frictionally mates with the rod under pressure from the rod so as to lock the shank and ring in a selected angular configuration relative to the head. The shank, in this manner, can be locked in a configuration selected from an infinite number of angular configurations with respect to the head. Once fully assembled in this manner, unless a part breaks into pieces, the shank cannot disengage from the capture ring and the head without disassembly of the device by reversing the process or breaking the parts.

OBJECTS AND ADVANTAGES OF THE INVENTION

Therefore, the objects in the present invention are: to provide a polyaxial bone screw having a bone implantable shank that can be locked in a fixed position relative to a head of the bone screw; to provide such a bone screw having a capture or retaining ring having a partial external hemispherical surface that seats within a partial internal spherical shaped chamber surface within and integrally formed with a head of the bone screw to form a ball and socket joint and wherein the shank is securable to the retaining ring; to provide such a bone screw wherein the shank has at least one spline that extends radially outward from a capture end thereof and wherein the retaining ring has a central bore that receives the capture end while a channel opening into the bore allows the spline to slide through the ring so as to pass above the ring, at which time the shank can be rotated a select number of degrees and further wherein the retaining ring has a capture recess that receives the spline on further downward or reverse movement along the axis of the shank relative to the retainer ring; to provide such a bone screw wherein the shank has an upwardly protruding radiused dome which has a radius that in one embodiment is substantially less than the radius of the external hemispherical surface on the retainer ring and that extends upwardly within the head chamber so as to reduce height of the screw head and further, is operably positioned so as to engage a rod member received in the head so as to receive downward pressure from the rod during assembly; to provide such a bone screw wherein a closure top is used to close a channel in the bone screw head after receiving the rod and to apply pressure to the rod member that in turn, exerts pressure on the dome of the shank so as to urge each spline into an abutting and tight relationship with the retaining ring and to urge the retaining ring both downwardly and radially outwardly, so that the external hemispherical surface on the retaining ring more completely contacts and frictionally engages the internal spherical surface within the chamber of the head thereby providing improved mechanical fixation to prevent further rotation of the shank relative to the head; to provide such a bone screw which has a comparatively low profile and which is comparatively light in weight; to provide such a bone screw that resists disassembly thereof except by removal of the closure top; to provide such a bone screw wherein the closure top can be removed by the surgeon should disassembly be desired at which time the entire structure can be easily and quickly disassembled and removed from the bone, if necessary; to provide such a bone screw wherein the shank is locked in position relative to the head during usage in a locked or fixed configuration; to provide such a bone screw wherein the shank cannot disassemble from the head and the retaining ring once the screw is fully assembled except if the closure top is removed and the device is disassembled by the surgeon; to provide such a bone screw which is easy to use and extremely effective for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of three elements of a polyaxial bone screw in accordance with the present invention, including a shank, a head, and a retaining ring.

FIG. 2 is an enlarged top plan view of the retaining ring.

FIG. 3 is an enlarged perspective view of the retaining ring.

FIG. 4 is an enlarged side elevational view of the retaining ring.

FIG. 5 is an enlarged bottom plan view of the retaining ring.

FIG. 6 is an enlarged cross-sectional view of the head, taken along line 6-6 of FIG. 1, illustrating the retaining ring being inserted into the head.

FIG. 7 is an enlarged cross-sectional view of the head similar to FIG. 6, showing the retaining ring seated in the head.

FIG. 8 is a cross-sectional view of a vertebra illustrating the shank implanted therein.

FIG. 12 is a cross sectional view of the head and a top plan view of the shank and ring corresponding to the positioning shown in FIG. 10.

FIG. 13 is a cross sectional view of the head and a top plan view of the shank and ring corresponding to the positioning shown in FIG. 11.

FIG. 15 is a fragmentary and partially exploded view of a complete polyaxial bone screw assembly, prior to final assembly and illustrating a rod received in the head and a closure top with a break-off head, prior to the closure top being rotatably inserted into the head.

FIG. 16 is a fragmentary and enlarged front elevational view of the bone screw assembly fully assembled and illustrating the head with the rod received therein and with the closure top fully inserted and biasing against the rod that in turn biases against the top of the shank.

FIG. 17 is an enlarged and fragmentary cross-sectional view of the bone screw assembly with rod inserted therein, taken along line 17-17 of FIG. 16.

FIG. 20 is a perspective view of a second modified embodiment of the present invention illustrating a cannulated shank having four splines and a hex tool engageable head for manipulating the shank.

FIG. 21 is a perspective view of a ring for use in accordance with the second modified embodiment of the invention and the shank of FIG. 20.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference number 1 generally represents a polyaxial bone screw apparatus or assembly in accordance with the present invention operably utilized by implantation into a vertebra 2 and in conjunction with a longitudinal member or rod 3 so as to operably secure the rod 3 in a fixed position relative with respect to the vertebra 2.

Figure 18:
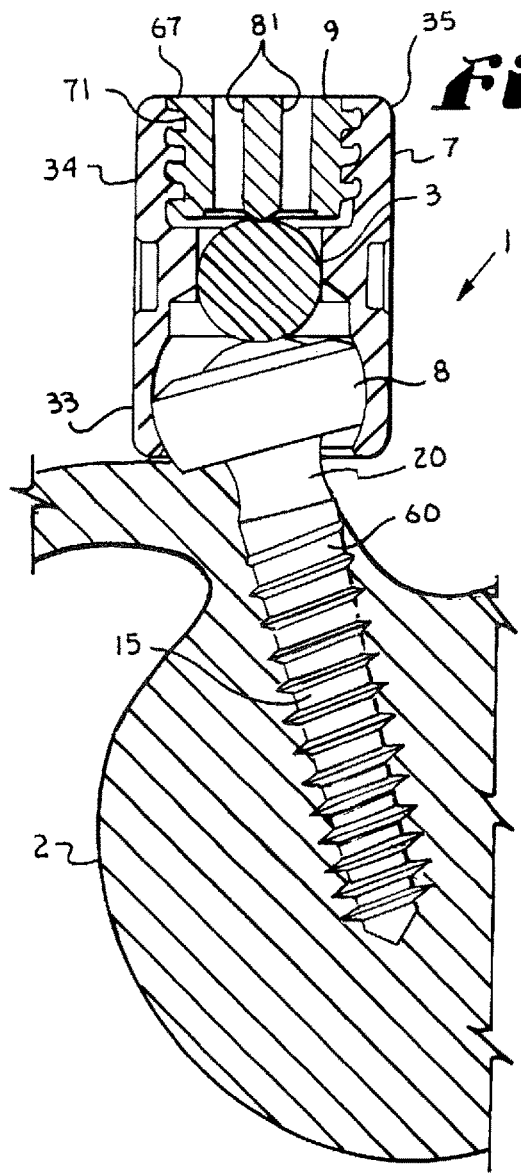
FIG. 18 is an enlarged cross-sectional view of the vertebra, head, rod and closure top, taken along line 18-18 of FIG. 17 showing the shank implanted in the vertebra and with the bone screw assembly in a completely assembled and operational configuration with the shank locked in an angled orientation with respect to the head.

The fully assembled bone screw assembly 1 comprises a shank 6, a head 7, a retainer ring 8 and a closure top 9. The shank 6 is perhaps best seen in FIGS. 1 and 8. The shank 6 is elongate and has a lower body 15 ending in a tip 16. The shank body 15 has a helically wound bone implantable thread 17 extending from near the tip 16 to near the top 18 of the body 15 and extending radially outward therefrom. During use, the body 15 utilizing the thread 17 is implanted into the vertebra 2, as is seen in FIG. 18. The shank 6 has an elongated axis of rotation generally identified by the reference letter A. It is noted that the reference to the words top and bottom as used herein refers to the alignment shown in the various drawings, as well as the normal connotations applied to such devices, and is not intended to restrict positioning of the assembly 1 in actual use.

Axially extending outward and upward from the shank body 15 is a neck 20 of reduced radius as compared to the adjacent top 18 of the body 15. Further extending axially and outwardly from the neck 20 is a capture end or structure 21 operably providing a connective or capture structure free from the bone or vertebra 2 for joining with the head 7. The capture structure 21 has a radially outer cylindrical surface 22. The cylindrical surface 22 has at least one non-helically wound and radially outward extending projection or spline 24 that extends beyond the surface 22. In the embodiment shown in FIGS. 1 through 18, the capture structure 21 has three such splines 24. The splines 24 are located near an upper end 25 of the shank 6 and are equally circumferentially centered and spaced thereabout so as to be centered at approximately 120 degree intervals relative to each other. Each of the splines 24 has a triangular shaped profile and a front wedge forming face 27 that slopes downwardly and radially inwardly from near the upper end 25 of the shank 6. Also located on the shank upper end 25 is a centrally located, axially extending and upwardly directed projection or dome 29 that is centrally radiused so as to have a first radius.

The shank upper end 25 still further includes at least one tool engagement aperture for engagement by a tool driving head (not shown) that is sized and shaped to fit into the apertures for both driving and rotating the shank 6 into the vertebra 2. In the illustrated embodiment, a pair of apertures 31 located in spaced relationship to each other, the dome 29 and the shank axis of rotation A are located on the shank upper end 25. The apertures 31 extend into the shank capture structure 21 parallel to the axis A. It is foreseen that various numbers of apertures, slots or the like may be utilized in accordance with the invention for engaging the driving tool of suitable and similar mating shape, or that the outer surface of the upper axial projection can be grooved or formed with a faceted surface that can be driven by a mating tool that goes over the surface.

The head 7 has a generally cylindrical shaped profile, as is seen in FIG. 1, although the head 7 is not a solid cylinder. The head 7 has a base 33 with a pair of upstanding arms 34 and 35 forming a U-shaped channel 38 between the arms 34 and 35 with a lower seat 39 having substantially the same radius as the rod 3 for operably snugly receiving the rod 3. Each of the arms 34 and 35 has an interior surface 41 that includes a partial helically wound guide and advancement structure 42. In the illustrated embodiment, the guide and advancement structure 42 is a partial helically wound flangeform which will mate under rotation with a similar structure on the closure top 9, as described below. However, it is foreseen that the guide and advancement structure 42 could alternatively be a V-shaped thread, a buttress thread, a reverse angle thread or other thread like or non-thread like helically wound advancement structures for operably guiding under rotation and advancing the closure top between the arms 34 and 35. Tool engaging apertures 44 are formed on the outsides of the arms 34 and 35 for holding the head 7 during assembly.

A chamber or cavity 47 is located within the head base 33 that opens upwardly into the U-shaped channel 38. The cavity 47 includes a partial spherical shaped surface 48, at least a portion of which forms a partial internal hemispherical seat 49 for the ring 8, as is described further below. A bore 52 further communicates between the cavity 47 and the bottom exterior of the base 33 and is coaxial with a rotational axis B of the head 7. The bore 52 at least partially defines a restrictive neck 54 that has a radius which is smaller than the radius of the ring 8, as will be discussed further below, so as to form a restrictive constriction at the location of the neck 54 relative to the retainer ring 8 to prevent the ring 8 from passing between the cavity 47 and the lower exterior of the head 7. A bevel 55 extends between the neck 54 and the bottom exterior of the base 33. The hemispherical shaped surface 48 has a second radius associated therewith.

The retainer ring 8 which is best seen in FIGS. 2 through 5 has an operational central axis which is the same as the elongate axis A associated with the shank 6, but when the ring 8 is separated from the shank 2, the axis of rotation is identified as axis C, such as in FIG. 4. The retainer ring 8 has a central bore 57 that passes entirely through the retainer ring 8 from a top surface 58 to a bottom surface 59 thereof. The bore 57 is sized and shaped to fit snugly but slidably over the shank capture structure cylindrical surface 22 in such a manner as to allow sliding axial movement therebetween under certain conditions, as described below. Three axially aligned channels 60 are spaced from the axis C and extend radially outward from the bore 57 and into the wall of the retainer ring 8 so as to form three top to bottom grooves or slots therein. Backs 61 of the channels 60 are the same radial distance from the axis C as the distance the outermost portion of the splines 24 extend from the axis A of the shank 6. The channels 60 are also circumferentially angularly spaced equivalent to and have a width that corresponds with the splines 24. In this manner, the shank capture structure 21 can be uploaded into the ring 8 by axially sliding the capture structure 21 through the ring central bore 57 whenever the splines 24 are aligned with the channels 60 or are in an aligned configuration, as seen in FIG. 12.

The retainer ring 8 also has three capture partial slots, receivers or recesses 62 which extend radially outward from the upper part the bore 57 and that do not extend the entire length from top to bottom of the retainer ring 8, but rather only open on the top surface 59 and extend partly along the height of the ring 8 thereof. The recesses 62 are sized and positioned and shaped to receive the splines 24 from above when the splines 24 are in a non-aligned configuration relative to the channels 60. That is, each of the recesses 62 has a width that approximates the width of the splines 24 and has a mating wedge engaging surface 64 that is shaped similar to the spline wedge forming faces 27, so that the splines 24 can be slidably received into the recesses 62 from above by axially translating or moving the shank 6 downward relative to the ring 8 when the splines 24 are positioned above the recesses 62 in a recess aligned configuration.

In some embodiments, the wedge engaging faces 64 slope slightly greater than the wedge forming faces 27 on the splines 24 so that there is additional outward wedging that takes place when the splines 24 are urged downwardly into the recesses 62, as further discussed below.

In this manner the shank capture structure 21 can be uploaded or pushed upwardly through the retainer ring central bore 57 so as to clear the top 58 of the retainer ring 8, rotated approximately 60 degrees and then downloaded or brought downwardly so that the splines 24 become located and captured in the recesses 62. Once the splines 24 are seated in the recesses 62 the shank 6 cannot move further axially downward relative to the ring 8. Preferably, the retainer ring 8 is constructed of a metal or other material having sufficient resilience and elasticity as to allow the ring 8 to radially expand slightly outward by downward pressure of the splines 24 on the recesses 62 under pressure from structure above, as will be discussed further below. This produces a slight outward radial expansion in the ring 8 at the location of the recesses 62.

The ring 8 has a radially outer partial hemispherical shaped surface 65 sized and shaped to mate with the partial spherical shaped surface 48 and having a third radius approximately equal to the second radius associated with the surface 48. The ring third radius is substantially larger than the first radius associated with the dome 29 and also substantially larger than the radius of the neck 54.

The longitudinal member or elongate rod 3 can be any of many different types of implants utilized in reconstructive spinal surgery and the like, but is normally a cylindrical elongate structure having a cylindrical surface 66 of uniform diameter. The rod 3 is preferably sized and shaped to snugly seat near the bottom of the U-shaped channel 38 and, during normal operation, will be positioned slightly above the bottom of the channel 38. In particular, the rod 3 normally engages the shank dome 29, as is seen in FIG. 16 and urges the dome 29 and, consequently, the shank 6 downwardly when the entire assembly 1 is fully assembled.

The closure top 9 can be any of the variety of different types of closure tops for use in conjunction with the present invention with suitable mating structure on the upstanding arms 34 and 35. The illustrated closure top 9 has a generally cylindrical shaped base 67 with an upwardly extending break-off head 68. The base 67 includes a helically wound guide and advancement structure 71 that is sized, shaped and positioned so as to engage the guide and advancement structure 42 on the arms 34 and 35 to allow the closure top 9 to be rotated into the head 7 and, in particular, to close the top of the U-shaped channel 38 to capture the rod 3, see FIG. 16, preferably without splaying of the arms 34 and 35. The closure top 9 also operably biases against the rod 3 by advancement and applying pressure to the rod 7 under torqueing, so that the rod 3 is urged downwardly against the shank dome 29. Downward biasing of the shank dome 29 operably produces a frictional engagement between the rod 3 and dome 29 and also urges the splines 24 downwardly to both bias downwardly and radially outwardly against the retainer ring 8, so as to snugly and frictionally seat the retainer ring external hemispherical surface 65 into and quite tightly against the partial internal spherical surface 48 of the head 7 and further so as to lock the shank 6 and retainer ring 8 in a fixed position relative to the head 7.

The closure top break-off head 68 is secured to the base 67 at a neck 73 that is sized and shaped so as to break away at a preselected torque that is designed to properly seat the retainer ring 8 in the head 7. The break-off head 68 includes an external faceted surface 75 that is sized and shaped to receive a conventional socket head of a driving tool (not shown) to rotate and torque the closure top 9. The break-off head 68 also includes a central bore 77 and grooves 78 for operably receiving the manipulating tools.

The closure top 9 also includes removal structure comprising a pair of off axis pass through apertures 81 that extend from top to bottom of the base 67. The apertures 81 are located parallel to an axis of rotation axis D of the closure top 9, but are radially spaced away therefrom. The apertures 81 become accessible from the top of the base 67 after the break-off head 68 breaks away from the base 67, as is seen in FIG. 18. The apertures 81 are designed to receive a tool having a face that mates with and is insertable into the apertures 81 for rotating the closure top base 67 subsequent to installation so as to provide for removal, if necessary.

While the embodiment illustrated in FIGS. 1 through 18 includes three splines 3, it is foreseen that a shank 6 with a single spline would be operable within the scope of the invention. However, in some embodiments additional splines 3 may provide a more even distribution of force upon the ring 8 and reduce the likelihood of failure because of hoop strain or the like. Paired and opposed splines in certain embodiments may provide a more even distribution of forces. While any number of splines are foreseen as possible for use under the present invention, the requirement that the splines must get smaller as their number gets larger, limits the maximum number at some point. However, the concept appears viable until that point is reached. It is also noted that additional channels and recesses allow the ring to be more elastic in certain embodiments.

When the polyaxial bone screw assembly 1 is placed in use in accordance with the invention the retainer ring 8 is normally first slid through the head U-shaped channel 38, as is shown in FIG. 6, and into and seated in the chamber 47, as is seen in FIG. 6. Thereafter, the retainer ring 8 is rotated 90 degrees so as to be coaxial with the head 7 and so that the retainer ring outer surface 65 snugly but slidably mates with the head interior spherical shaped surface 48, as is seen in FIG. 7.

Figure 9:
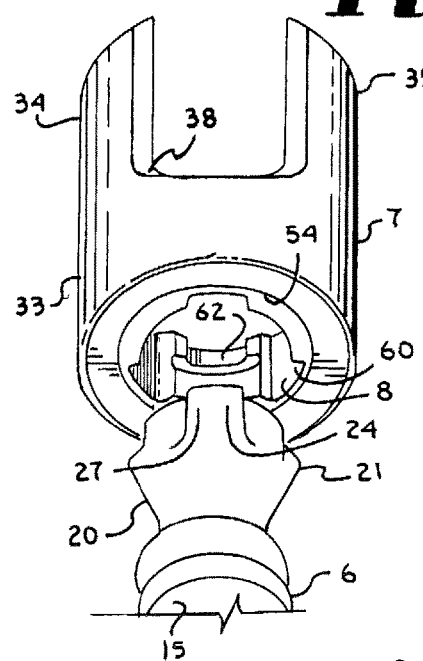
FIG. 9 is an enlarged and fragmentary perspective view of the shank, head and retainer ring during assembly and just prior to the retainer ring being placed over the shank.
Figure 10:
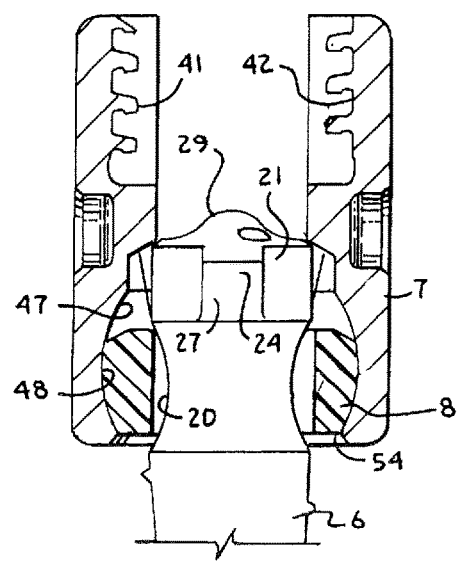
FIG. 10 is an enlarged, fragmentary and perspective cross-sectional view of the head similar to FIG. 6, illustrating splines on a capture end of the shank that have been inserted through channels in the retainer ring and are positioned upwardly in the head above the retainer ring.
Figure 11:
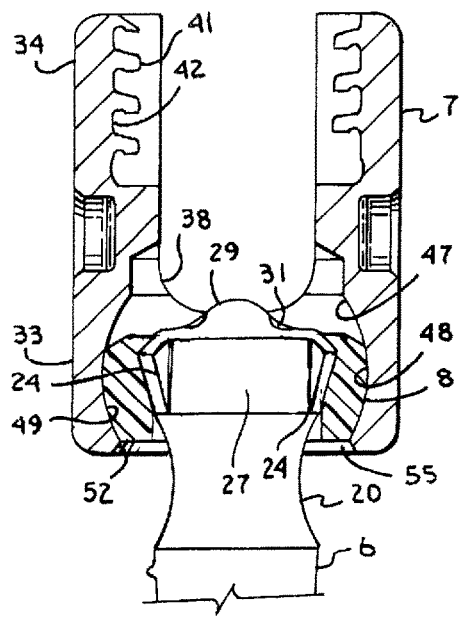
FIG. 11 is a cross-sectional view of the head, similar to FIG. 10, showing the upper capture end of the shank with the splines lowered into receiving recesses in the ring and positioned therein.
Figure 14:
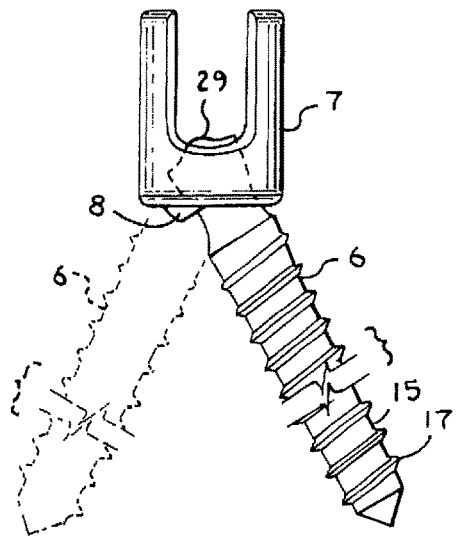
FIG. 14 is a side elevational view of the head, ring and shank, illustrating the shank swinging or rotating from one position shown in solid lines to a second position shown in phantom lines.

With reference to FIGS. 9, 10, and 12 the ring 8 in the head 7 is slid over the shank capture structure 21 so that the splines 24 slide upwardly through and above respective channels 60 so that the splines 24 are then located, at least partially, in the U-shaped channel 38 and chamber 47 above the retainer ring 8, as is shown in FIG. 10. The shank 6 is then rotated 60 degrees relative to the head about the axis A and the translational direction of the shank 6 is reversed so that it goes downwardly or axially with respect to the head 7, as is seen in FIGS. 11 and 13 and the splines 24 enter the recesses 62. At this point there is no substantial outward or downward pressure on the retainer ring 8 and so the retainer ring 8 is easily rotatable along with the shank 6 within the chamber 47 and such rotation is of a ball and socket type limited by engagement of the shank neck 20 with the ring restrictive neck 54. Rotation is shown in FIG. 14 where it is illustrated that the shank 6 can be rotated through a substantial angular rotation relative to head 7, both from side to side and from front to rear so as to substantially provide a universal or ball joint wherein the angle of rotation is only restricted by engagement of the neck 20 with the neck 54 on the head 7.

The assembly 1 is then normally screwed into a bone, such as vertebra 2, by rotation of the shank 6 using a suitable driving tool (not shown) that operably drives and rotates the shank 6 by engagement thereof at the apertures 31. The relative position of the shank 6 is shown in FIG. 8 with a phantom vertebra 2. Normally, the head 7 and ring 8 are assembled on the shank 6 before placing the shank 6 in the vertebra 2, but in certain circumstances, the shank 6 can be first implanted with the capture structure 21 extending proud to allow assembly and then the shank 6 can be further driven into the vertebra 2.

A rod 3 is eventually positioned within the head U-shaped channel 38, as is seen in FIG. 15, and the closure top 9 is then inserted into and advanced between the arms 34 and 35 so as to bias or push against the rod 3. The break-off head 68 of the closure top 9 is torqued to a preselected torque, for example 90 inch pounds, to urge the rod 3 downwardly. The shank dome 29, because it is radiused and sized to extend upwardly into the U-shaped channel 38, is engaged by the rod 3 and pushed downwardly when the closure top 9 pushes downwardly on the rod 3, as is seen in FIG. 16.

The downward pressure on the shank 6 in turn urges the splines 24 downwardly which exerts both a downward and outward thrust on the retainer ring 8, as is seen in the configuration shown in FIG. 17. The polyaxial bone screw assembly 1 including rod 3 and shown positioned in a vertebra 2 is illustrated in FIG. 18. The axis A of the bone screw shank 6 is illustrated as not being coaxial with the axis B of the head 7 and the shank 6 is locked in this angular locked configuration. Other angular configurations can be achieved, as required during installation surgery due to positioning of the rod 3 or the like.

If removal of the assembly 1 is necessary, the assembly 1 can be disassembled by using a driving tool mating with the closure top apertures 81 to rotate the base 67 and reverse the advancement thereof in the head 7 and then disassembly of the remainder of the assembly 1 in reverse mode in comparison to the procedure described above for assembly.

Figure 19:
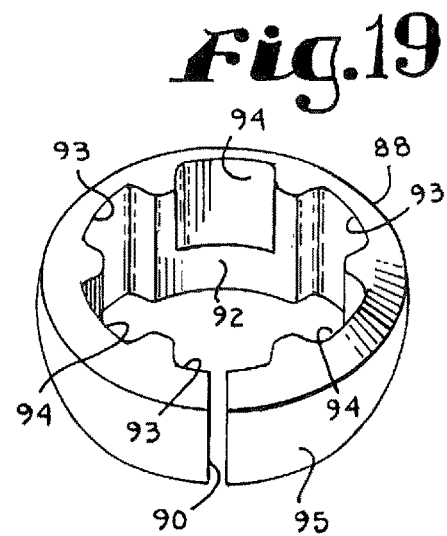
FIG. 19 is a perspective view of a modified retainer ring of a first modified embodiment in accordance with the present invention.

Illustrated in FIG. 19 is a second embodiment of a retainer ring 88 in accordance with the present invention. The retainer ring 88 is quite similar to the retainer ring 8 of the previous embodiment except that it is noncontinuous and has a radially extending space or gap 90 from top to bottom along one side thereof. The gap 90 allows for expansion without requiring stretching of the material of construction of the ring 88, as is the case with the previous embodiment. The ring 88 includes a central bore 92, spline channels 93 and spline receivers 94 which are all similar to the similar structures described for the previous embodiment. The retainer ring 88 also has a partial hemispherical shaped surface 95 on the outer side thereof.

Illustrated in FIGS. 20 and 21 are elements of a third embodiment of the present invention including a shank 106 and a capture ring 107 which are used otherwise in the same manner as has been described in the first embodiment and, in particular, with a head such as head 7 which is not further described herein. The shank 106 is similar to the shank 6 in that it has a body 110 with a helically round thread 111 thereon and a capture structure 114 joined to the body 110 by a neck 115. The principle differences between the present embodiment and the first embodiment is that the capture structure 114 includes four splines 120 that are similar in shape to the splines 24 of the first embodiment, but the splines 120 are centered and located at 90 degrees from one another such that there is a pairing of opposed splines 120 and the dome of the prior embodiment is replaced with an axial extension 122. Each of the splines 120 includes a wedge face 121. The extension 122 has a faceted surface 123 that extends parallel to the axis of the shank 106 and that is sized and shaped to receive a hex head driving tool (not shown) for driving the shank 106 into bone. The extension 123 also has a radiused upper surface 124. The shank 106 also has an axial extending cannulation or bore 125 that extends entirely through the length of the shank 106.

The capture ring 107, shown in FIG. 21, is otherwise similar to the retainer ring 8 except that it includes a set of four channels 126 and four recesses 127 that are sized shaped and positioned so as with respect to the channels 126 to allow the splines 120 to slidingly pass upwardly through and with respect to the recesses 127 to capture and receive the splines 120, as they move axially downwardly. The ring 107 has a partial hemispherical outer surface 129 that mates with the corresponding surface in the head 7 in the manner described for the first embodiment.

It is to be understood that while certain forms of the present invention have been illustrated and described herein, it is not to be limited to the specific forms or arrangement of parts described and shown.

What is claimed is:

1. A pivotal bone screw assembly for securing a longitudinal stabilization member to a bone of a patient via a closure, the pivotal bone screw assembly comprising:
    a head member having a base defining a cavity with a bottom opening in communication with a bottom surface of the base, and a pair of integral arms extending upward from the base to define a channel in communication with the cavity and having interior surfaces configured for receiving the longitudinal stabilization member therebetween, the cavity having an internal seating surface adjacent the bottom opening;
    an anchor member having a proximal end portion, a distal end portion, and a central opening extending entirely through the anchor member along a central longitudinal axis of the anchor member and opening onto a top end of the proximal end portion and a bottom end of the distal end portion, the distal end portion comprising an implant portion configured to be implanted into the bone; and
    a retainer configured to be disposed within the cavity prior to the anchor member and configured to pivot with respect to the internal seating surface, the retainer having a top surface, a bottom surface, and an outer surface operable to pivotally engage the internal seating surface, a central bore extending from the top surface to the bottom surface with an inner surface operable to releasably engage the proximal end portion of the anchor member so that a downward force applied to the top end of the anchor member is required to hold the proximal end portion down within the retainer, and a through-and-through gap extending from the top surface to the bottom surface on the retainer,
    wherein the retainer is configured to capture the proximal end portion of the anchor member and hold the proximal end portion in spaced relation with respect to the internal seating surface while allowing for pivotal motion of the anchor member relative to the head member prior to locking the pivotal bone screw assembly with the closure, and
    wherein upon locking of the pivotal bone screw assembly with the closure, the retainer remains spaced apart from the longitudinal stabilization member received in the channel of the head member.

2. The pivotal bone screw assembly of claim 1, wherein the internal seating surface of the cavity further comprises a partial hemispherical surface.

3. The pivotal bone screw assembly of claim 1, wherein, when the retainer has captured the proximal end portion of the anchor member, the proximal end portion of the anchor member extends above the top surface of the retainer.

4. The pivotal bone screw assembly of claim 1, wherein the top end of the proximal end portion of the anchor member further comprises a radiused upper surface with the central opening exiting therethrough.

5. The pivotal bone screw assembly of claim 1, wherein, in the course of causing the proximal end portion of the anchor member to be captured by the retainer, the proximal end portion of the anchor member is bottom loaded into the head member.

6. The pivotal bone screw assembly of claim 1, wherein the central opening of the anchor member is unthreaded along the distal end portion.

7. The pivotal bone screw assembly of claim 1, wherein the implant portion of the distal end portion of the anchor member further comprises an external helically wound thread.

8. The pivotal bone screw assembly of claim 1, wherein the implant portion of the distal end portion of the anchor member further comprises a threaded shank.

9. The pivotal bone screw assembly of claim 1, wherein the outer surface of the retainer further comprises an outer partial hemispherical shaped surface that allows the retainer to pivot with respect to the head member.

10. The pivotal bone screw assembly of claim 1, further comprising the closure, wherein the closure is configured to cooperate with the channel of the head member to retain the longitudinal stabilization member within the channel.

11. The pivotal bone screw assembly of claim 10, wherein the closure further comprises a closure top configured to engage the interior surface of the pair of integral arms to urge the longitudinal stabilization member into a locked position within the head member.

12. The pivotal bone screw assembly of claim 1, wherein the pair of integral arms of the head member have exterior surfaces with tool attachment structures formed therein.

13. The pivotal bone screw assembly of claim 12, wherein the tool attachment structures have outwardly-facing recessed planar surfaces that are parallel with respect to each other.

14. The pivotal bone screw assembly of claim 1, wherein the interior surfaces of the pair of integral arms further include an internal helically wound guide and advancement structure.

15. The pivotal bone screw assembly of claim 1, wherein the internal seating surface of the cavity is spherical.

16. The pivotal bone screw assembly of claim 1, wherein the retainer, after being disposed within the cavity and capturing the proximal end portion of the anchor member, is inhibited from moving in a vertical direction along a longitudinal axis of the head member prior to the pivotal bone screw assembly being locked by the closure.

17. The pivotal bone screw assembly of claim 1, wherein the anchor member is configured to be implanted into the bone prior to the proximal end portion being captured within the cavity of the head member by the retainer.

18. The pivotal bone screw assembly of claim 1, wherein the anchor member and the head member are configured to be connected and implanted into the bone prior to the closure being inserted into the channel of the head member.

19. The pivotal bone screw assembly of claim 1, wherein the anchor member further includes a neck portion between the proximal end portion and the distal end portion, the neck portion having smooth, non-threaded outer surface.

20. The pivotal bone screw assembly of claim 19,
wherein the implant portion of the distal end portion of the anchor member further comprises an external helically wound thread, and
wherein a largest outer diameter of the external helically wound thread is greater than an outer diameter of the neck portion.

21. The pivotal bone screw assembly of claim 19, wherein the neck portion further comprises an inwardly-concave curvate profile configured to provide for increased angulation of the anchor member relative to the head member.

22. The pivotal bone screw assembly of claim 11, wherein the closure top has one of a solid central core and a solid closed off central bottom surface configured to engage the longitudinal stabilization member positioned within the channel.

23. The pivotal bone screw assembly of claim 1, wherein the central opening of the anchor member is laterally closed along an entire length thereof and has a constant diameter at least along the distal end portion of the anchor member and including a bottom end opening defined by the central opening opening onto the bottom end of the distal end portion.

24. The pivotal bone screw assembly of claim 5, wherein the proximal end portion is slidably engaged with the retainer.

25. A pivotal bone screw assembly for securing a longitudinal stabilization member to a bone of a patient, the pivotal bone screw assembly comprising:
a head member having a base defining a cavity with a bottom opening in communication with a bottom surface of the base, and a pair of integral arms extending upward from the base to define a channel in communication with the cavity and having interior surfaces configured for receiving the longitudinal stabilization member therebetween, the cavity having an internal seating surface that narrows toward the bottom opening;
an anchor member having a proximal end portion, a distal end portion, and a central opening extending entirely through the anchor member along a central longitudinal axis of the anchor member and opening onto a top end of the proximal end portion and onto a bottom end of the distal end portion to define a bottom end opening, the central opening being closed laterally along an entire length thereof and having a constant diameter at least along the distal end portion of the anchor member and including the bottom end opening, the distal end portion comprising an implant portion configured to be implanted into the bone; and
a retainer configured to be disposed within the cavity prior to the anchor member and configured to pivot with respect to the internal seating surface of the cavity, the retainer having an outer surface operable to engage the internal seating surface, a central bore with an inner surface operable to engage the proximal end portion of the anchor member, and a through-and-through gap extending from a top surface to a bottom surface on the retainer,
wherein the retainer is configured to capture the proximal end portion of the anchor member and releasably hold the proximal end portion so that a downward force applied to the top end of the proximal end portion of the anchor member is required to hold the proximal end portion down within the retainer, wherein, when the proximal end portion has been captured by the retainer and the pivotal bone anchor assembly is in an unlocked state, the proximal end portion is in spaced relation to the internal seating surface of the cavity while allowing for pivotal motion of the anchor member relative to the head member, and
wherein the anchor member further includes a smooth, non-threaded neck portion between the proximal end portion and the distal end portion.

26. The pivotal bone screw assembly of claim 25, wherein the neck portion further comprises an inwardly-concave curvate profile configured to provide for increased angulation of the anchor member relative to the head member.

27. The pivotal bone screw assembly of claim 25, wherein the neck portion has an outer diameter that is less than a largest outer diameter of the distal end portion to provide for increased angulation of the anchor member relative to the head member.

28. The pivotal bone screw assembly of claim 25, wherein the retainer is spaced apart from the longitudinal stabilization member when the proximal end portion has been captured by the retainer and the longitudinal stabilization member is positioned in the channel.

29. The pivotal bone screw assembly of claim 25, wherein the top end of the proximal end portion of the anchor member further comprises a radiused upper surface with the central opening exiting therethrough.

30. The pivotal bone screw assembly of claim 25, wherein, when the retainer has captured the proximal end portion of the anchor member, the top end of the proximal end portion of the anchor member extends above the top surface of the retainer.

31. A pivotal bone screw assembly for securing a longitudinal stabilization member to a bone of a patient, the pivotal bone screw assembly comprising:
a head member having a base defining a cavity with a bottom opening in communication with a bottom surface of the base, and a pair of integral arms extending upward from the base to define a channel in communication with the cavity and having interior surfaces configured for receiving the longitudinal stabilization member therebetween, the cavity having an internal seating surface that narrows toward the bottom opening;
an anchor member having a proximal end portion, a distal end portion, and a central opening extending entirely through the anchor member along a central longitudinal axis of the anchor member and opening onto a top end of the proximal end portion and a bottom end of the distal end portion, the distal end portion comprising an implant portion configured to be implanted into the bone; and a retainer configured to be disposed within the cavity prior to the anchor member and configured to pivot with respect to the internal seating surface, the retainer having an outer surface operable to engage the internal seating surface, a central bore with an inner surface operable to engage the proximal end portion of the anchor member, and a through-and-through gap extending from a top surface to a bottom surface on the retainer, wherein the retainer is configured to capture the proximal end portion of the anchor member and releasably hold the proximal end portion so that a downward force applied to the top end of the proximal end portion of the anchor member is required to hold the proximal end portion down within the retainer, wherein, when the proximal end portion has been captured by the retainer and the pivotal bone anchor assembly is in an unlocked state, the proximal end portion is in spaced relation to the internal seating surface while allowing for pivotal motion of the anchor member relative to the head member, and wherein the anchor member further includes a smooth, non-threaded neck portion between the proximal end portion and the distal end portion.

32. The pivotal bone screw assembly of claim 31, wherein the neck portion further comprises an inwardly-concave curvate profile configured to provide for increased angulation of the anchor member relative to the head member.

33. The pivotal bone screw assembly of claim 31, wherein the neck portion has an outer diameter that is less than a largest outer diameter of the distal end portion to provide for increased angulation of the anchor member relative to the head member.

34. The pivotal bone screw assembly of claim 31, wherein the retainer is spaced apart from the longitudinal stabilization member when the proximal end portion has been captured by the retainer and the longitudinal stabilization member is positioned in the channel.

35. The pivotal bone screw assembly of claim 31, wherein the top end of the proximal end portion further comprises a radiused upper surface with the central opening exiting therethrough.

36. The pivotal bone screw assembly of claim 31, wherein, when the retainer has captured the proximal end portion of the anchor member, the top end of the proximal end portion of the anchor member extends above the top surface of the retainer.

37. A pivotal bone screw assembly for securing a longitudinal stabilization member to a bone of a patient via a closure, the pivotal bone screw assembly comprising:

a head member having a base defining a cavity with a bottom opening in communication with a bottom surface of the base, and a pair of integral arms extending upward from the base configured to define a channel in communication with the cavity and having interior surfaces for receiving the longitudinal stabilization member therebetween, the cavity having an internal seating surface that narrows toward the bottom opening;

an anchor member having a proximal end portion, a distal end portion, and a central opening extending entirely through the anchor member along a central longitudinal axis of the anchor member and opening onto a top end of the proximal end portion and onto a bottom end of the distal end portion to define a bottom end opening, the central opening being closed laterally along an entire length thereof and having a constant diameter at least along the distal end portion of the anchor member and including the bottom end opening, the distal end portion comprising an implant portion configured to be implanted into the bone; and a retainer configured to be disposed within the cavity prior to the anchor member and configured to pivot with respect to the internal seating surface, the retainer having a top surface, a bottom surface, and an outer surface operable to engage the internal seating surface, a central bore extending from the top surface to the bottom surface with an inner surface operable to engage the proximal end portion of the anchor member, and a through-and-through gap extending from the top surface to the bottom surface on the retainer, wherein upon movement of the proximal end portion of the anchor member relative to the retainer in a first direction, the retainer captures the proximal end portion of the anchor member and, prior to locking the pivotal bone screw assembly with the closure, holds the proximal end portion in spaced relation to the internal seating surface while allowing for pivotal motion of the anchor member relative to the head member, as well as relative motion between the proximal end portion and the retainer in at least one second direction, and wherein upon locking the pivotal bone screw assembly with the closure, the retainer remains spaced apart from the longitudinal stabilization member received in the channel.

* * * * *